(12) United States Patent
Chang et al.

(10) Patent No.: US 11,947,035 B2
(45) Date of Patent: Apr. 2, 2024

(54) FEATURE ENHANCEMENT AND DATA AUGMENTATION METHOD, AND MOTION DETECTION DEVICE THEREOF

(71) Applicant: Wistron Corporation, New Taipei (TW)

(72) Inventors: Hsuan-Tsung Chang, New Taipei (TW); Hao-Gong Chou, New Taipei (TW)

(73) Assignee: Wistron Corporation, New Taipei (TW)

( * ) Notice: Subject to any disclaimer, the term of this patent is extended or adjusted under 35 U.S.C. 154(b) by 491 days.

(21) Appl. No.: 17/233,580

(22) Filed: Apr. 19, 2021

(65) Prior Publication Data

US 2022/0244353 A1 Aug. 4, 2022

(30) Foreign Application Priority Data

Feb. 3, 2021 (TW) .................. 110103935

(51) Int. Cl.
*G01S 7/41* (2006.01)
*G01S 7/35* (2006.01)
*G06T 5/20* (2006.01)
*G06T 5/70* (2024.01)

(52) U.S. Cl.
CPC ............... *G01S 7/415* (2013.01); *G06T 5/20* (2013.01); *G06T 5/70* (2024.01); *G01S 7/356* (2021.05); *G06T 2207/10044* (2013.01)

(58) Field of Classification Search
CPC .......... G01S 13/88; G01S 7/356; G01S 7/415; G06T 5/20; G06T 5/002; G06T 2207/10044
See application file for complete search history.

(56) References Cited

U.S. PATENT DOCUMENTS

| | | | | |
|---|---|---|---|---|
| 5,442,462 A | * | 8/1995 | Guissin | G06T 5/002 |
| | | | | 358/463 |
| 5,771,318 A | * | 6/1998 | Fang | G06T 5/20 |
| | | | | 382/269 |
| 5,799,111 A | * | 8/1998 | Guissin | H04N 19/86 |
| | | | | 358/463 |
| 7,272,431 B2 | * | 9/2007 | McGrath | A61B 5/0507 |
| | | | | 600/509 |

(Continued)

FOREIGN PATENT DOCUMENTS

CN 109394229 A 3/2019

OTHER PUBLICATIONS

Rivera, "Radar-Based Fall Detection Exploiting Time-Frequency Features", Jul. 9, 2014.

(Continued)

*Primary Examiner* — Peter M Bythrow
(74) *Attorney, Agent, or Firm* — Winston Hsu

(57) ABSTRACT

A feature enhancement and data augmentation method for detecting at least one action of at least one tested subject is provided. The feature enhancement and data augmentation method includes obtaining at least one spectrogram; and performing a feature enhancement processing on the at least one spectrogram, to enhance at least one feature corresponding to at least one action in the at least one spectrogram and generate at least one feature enhanced spectrogram. The feature enhancement processing comprises a directional filtering.

20 Claims, 9 Drawing Sheets

(56) References Cited

U.S. PATENT DOCUMENTS

| | | | | |
|---|---|---|---|---|
| 7,567,200 | B1* | 7/2009 | Osterweil | G01S 13/56 342/28 |
| 7,916,066 | B1* | 3/2011 | Osterweil | A61B 5/1117 382/115 |
| 8,454,528 | B2* | 6/2013 | Yuen | A61B 5/0205 600/407 |
| 9,103,899 | B2* | 8/2015 | Hyde | G01S 13/0209 |
| 10,984,646 | B2* | 4/2021 | Schwab | G08B 25/009 |
| 11,660,023 | B2* | 5/2023 | Dvash | G01S 13/88 73/865.4 |
| 2006/0020203 | A1* | 1/2006 | Tamura | G06T 5/20 600/437 |
| 2010/0272340 | A1* | 10/2010 | Bar-Aviv | G06T 5/20 382/262 |
| 2013/0051674 | A1* | 2/2013 | Goossens | G06T 7/10 382/173 |
| 2013/0176158 | A1* | 7/2013 | Kim | G01S 13/10 341/166 |
| 2015/0379767 | A1* | 12/2015 | Inoue | G06T 5/20 382/154 |
| 2016/0063681 | A1* | 3/2016 | Esaki | G06T 5/00 382/199 |
| 2016/0377704 | A1* | 12/2016 | Harash | G01S 13/0209 342/21 |
| 2017/0131395 | A1* | 5/2017 | Reynolds | G01S 13/56 |
| 2018/0061013 | A1* | 3/2018 | Guo | G06T 5/002 |
| 2019/0139389 | A1* | 5/2019 | White | G08B 21/0415 |
| 2019/0216393 | A1* | 7/2019 | Baheti | H01L 23/66 |
| 2019/0219687 | A1* | 7/2019 | Baheti | G01S 7/415 |
| 2021/0158525 | A1* | 5/2021 | Iwase | G06T 7/97 |

OTHER PUBLICATIONS

Park, "SpecAugment: A simple data augmentation method for automatic speech recognition",Apr. 18, 2019.

Nithin Rao Koluguri, "Spectrogram Enhancement Using Multiple Window Savitzky-Golay(MWSG) Filter for Robust Bird Sound Detection",May 23, 2017.

Fok Hing Chi Tivive et al., A Human Gait Classification Method Based on Radar Doppler Spectrograms, EURASIP Journal on Advances in Signal Processing, vol. 2010, Article ID 389716, 2010, pp. 1-12, Hindawi Publishing Corporation, doi:10.1155/2010/389716, XP055869834.

* cited by examiner

FEATURE ENHANCEMENT AND DATA AUGMENTATION METHOD, AND MOTION DETECTION DEVICE THEREOF

BACKGROUND OF THE INVENTION

1. Field of the Invention

The present disclosure relates to a feature enhancement and data augmentation method and action detection device thereof, and more particularly, to a feature enhancement and data augmentation method and action detection device thereof capable of enhancing a feature of a falling action in a spectrogram to avoid false alarms, and increasing the amount of falling data via data augmentation algorithm to strengthen model generalization capability.

2. Description of the Prior Art

For current action detection technology, the action detection technology may determine whether the tested subject (such as the elderly, the patient or the child) has fallen, slipped or collided according to the rapid movement of the tested subject, thereby providing an alarm to inform the caregiver of the tested subject. Falling detection using continuous radar waves is non-imaging type, has good privacy, and may be more user-friendly in addition to long-term monitoring.

In this case, a spectrogram of a potential falling action has random vibration-like noise disturbances, and the main feature for distinguishing falling action and non-falling action is differences in spectrogram energy distribution. However, features of falling actions and some non-falling actions are similar in the spectrogram, and the model is still prone to generate false alarms even after training.

In addition, a part of the training set data is the actual data collected in the case field, and another part is falling data simulated in the laboratory. However, the falling data is difficult to collect, and the simulated self-falling action also results in a certain degree of risk, so the training set data is distributed quite unevenly (falling actions are much less than non-falling actions), so that the weight for the model to learn falling feature may be lower.

Therefore, it is necessary to improve the prior art.

SUMMARY OF THE INVENTION

It is therefore an objective of the present disclosure to provide a feature enhancement and data augmentation method and action detection device thereof capable of enhancing a feature of a falling action in a spectrogram to avoid false alarms, and increasing the amount of falling data via data augmentation algorithm to strengthen model generalization capability.

The present disclosure provides a feature enhancement and data augmentation method for detecting at least one action of at least one tested subject is provided. The feature enhancement and data augmentation method includes obtaining at least one spectrogram; and performing a feature enhancement processing on the at least one spectrogram, to enhance at least one feature corresponding to at least one action in the at least one spectrogram and generate at least one feature enhanced spectrogram. The feature enhancement processing comprises a directional filtering.

The present disclosure further provides an action detection device. The action detection device includes a processor, for executing a program; and a storage unit, coupled to the processor, for storing the program. The program is utilized for instructing the processor to perform following steps of obtaining at least one spectrogram; and performing a feature enhancement processing on the at least one spectrogram, to enhance at least one feature corresponding to at least one action in the at least one spectrogram and generate at least one feature enhanced spectrogram. The feature enhancement processing comprises a directional filtering.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
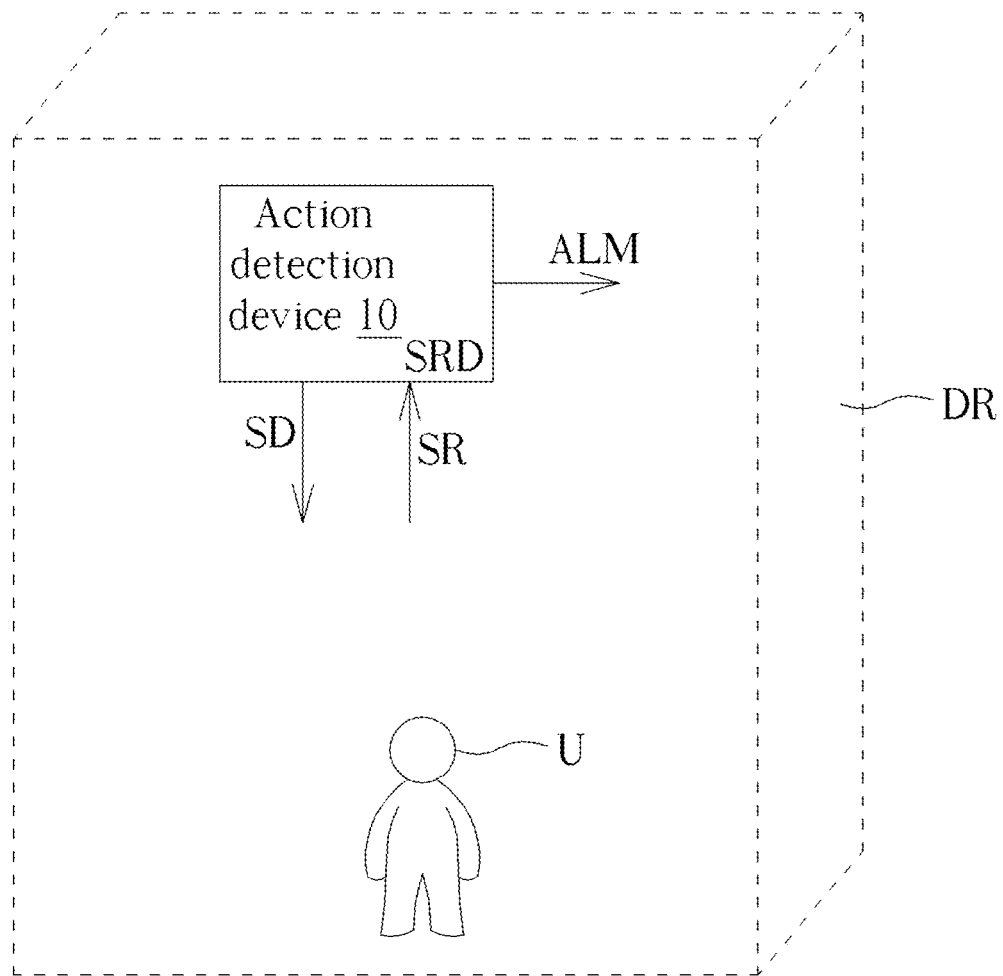
FIG. 1 is a schematic diagram of an action detection device and a field according to an embodiment of the present disclosure.

Please refer to FIG. 1, which is a schematic diagram of an action detection device 10 and a field DR according to an embodiment of the present disclosure. The action detection device 10 transmits at least one radio-frequency (RF) detection signal SD to the field DR, and receives at least one reflected RF signal SR from the field DR. In this embodiment, the action detection device 10 includes a processor, a transceiver circuit, and a storage unit. The processor is electrically connected to the transceiver circuit and the storage unit, respectively. The processor may be a microprocessor or an application-specific integrated circuit (ASIC). The transceiver circuit is a radar RF transceiver. The RF transceiver includes at least one transmitting antenna and/or at least one receiving antenna, an oscillator, a mixer, a digital to analog converter (DAC)0 an analog to digital converter (ADC), etc. The storage unit may be any data storage device for storing a code. The processor reads and executes the code.

In the present embodiment, the action detection device 10 performs signal processing on the reflected RF signal SR to obtain the raw signal SRD. In the present embodiment, the transceiver circuit of the action detection device 10 is a radar transceiver circuit, and coupled to the processor. The transceiver circuit receives at least one radar reflected RF detection signal SD, and processes the at least one radar reflected RF signal SR to obtain the raw signal SRD. More specifically, the mixer of the radar RF circuit performs down-conversion on the reflected RF signal SR (the radar reflected RF signal SR) to obtain an analog raw signal SRA. Then, the analog to digital converter of the radar RF circuit samples the analog raw signal SRA to obtain the raw signal SRD. In the present embodiment, the raw signal SRD represents Doppler components of the reflected RF signal SR in response to any body action in the field DR. Thus, the action detection device 10 determines whether a tested subject (e.g., a detected object U) in the field DR occurs a specific action according to the raw signal SRD, and provides an alarm ALM corresponding to the specific operation accordingly.

In the present embodiment, the action detection device 10 is a continuous wave (CW) radar or frequency modulated continuous wave (FMCW) radar. The field DR is the detected field of the action detection device 10. The specific action may be falling action, getting up action, rehabilitation action, training action, or other actions. The action detection device 10 may be installed in a space with only one single detected target, such as a room of an elderly living alone, a single room in a nursing center, etc.

In another embodiment of the present disclosure, the action detection device 10 is a frequency modulated continuous wave radar. The field DR is the detected field of the action detection device 10. The action detection device 10 (the frequency modulated continuous wave radar) may be installed in a space with multiple detected targets, such as a gym, indoor stadium, multi-person room in a nursing home and the like. The specific action may be respective falling action, getting up action, rehabilitation action, training action, or other actions of the multiple detected targets.

Figure 2:
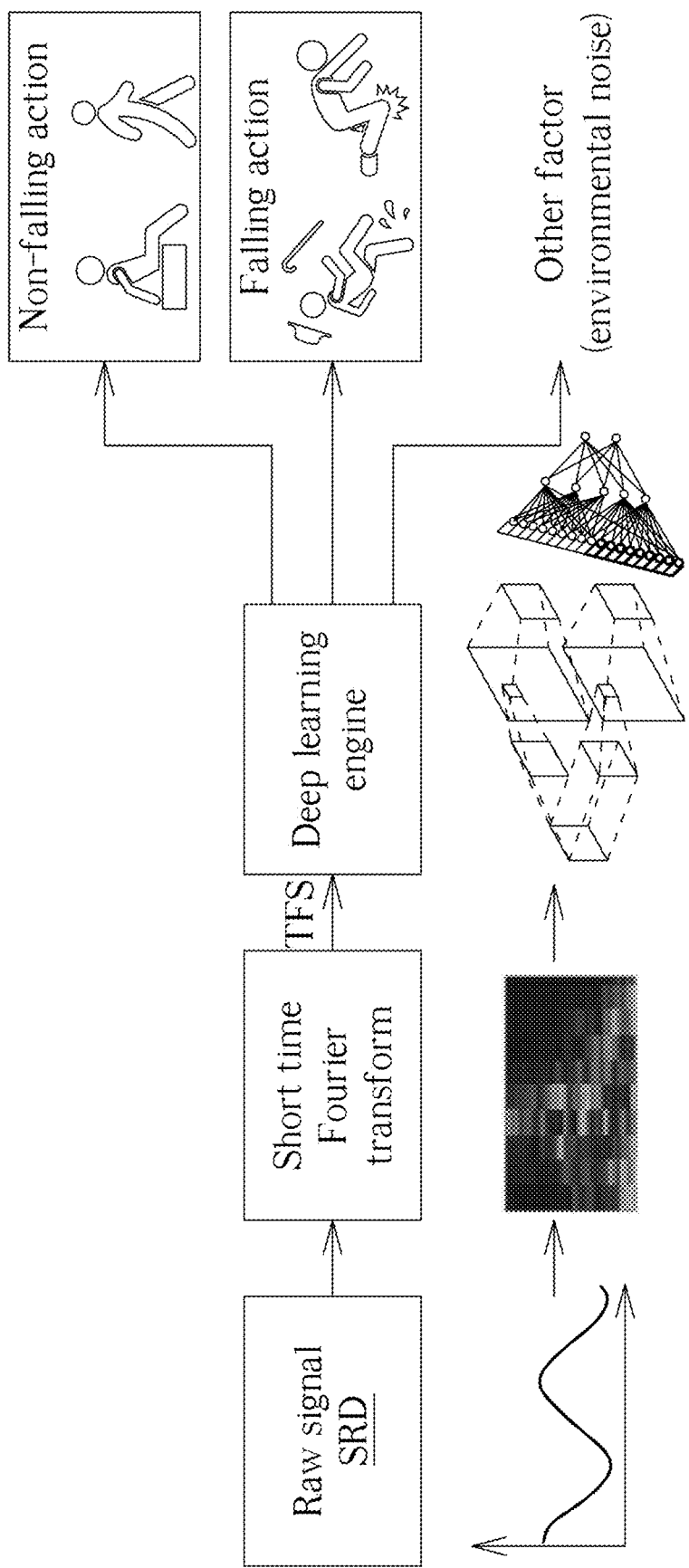
FIG. 2 is a schematic diagram of operations of the action detection device according to an embodiment of the present disclosure.

In this case, please refer to FIG. 2, which is a schematic diagram of operations of the action detection device 10 according to an embodiment of the present disclosure. As shown in FIG. 2, after obtaining the raw signal SRD through, for example, a continuous wave radar, the action detection device 10 performs short time Fourier transform (STFT) on the raw signal SRD, thereby obtaining a spectrogram TFS of frequency energy distribution of the raw signal SRD in each time interval. Since a time interval of a falling action having intensive energy change in a spectrogram is about 1.5-3 seconds, each spectrogram TFS after the short time Fourier transform is set to have each time interval as 3.2 seconds, in order to cover whole falling action. When there is an action change, frequency component of a spectrogram will strong disturbance. The present embodiment calculates power spectrum density between 100 Hz to 250 Hz in a sample interval, and defines a point with strongest energy (e.g., greater than 35 watts) as an energy burst point, i.e. a point with dramatic action change. Then, the present embodiment takes the energy burst point as a center to sample leftward and rightward (i.e. an time interval of 3.2 seconds with the energy burst point as the center) to obtain the spectrogram TFS for detecting potential falling action.

Next, a properly trained deep learning engine may identify the spectrogram TFS of potential falling action, to determine the spectrogram TFS is corresponding falling action such as bed falls, stumbling, slipping, etc., or non-falling action such as sitting, traveling, waving, etc., or other factors (e.g. environmental noise such as fan rotation, curtain swinging, etc.). If the action detection device 10 does not detect a getting up action within a period of time (e.g., 12 seconds) after determining a falling action, the action detection device 10 generates the alarm ALM to notify the family or medical personnel (the alarm ALM may be a warning sound directly or a warning signal transmitted to another device).

In this case, the spectrogram TFS of potential falling action has random vibration-like noise disturbances, and the main feature for distinguishing falling action and non-falling action is differences in spectrogram energy distribution. That is, because of the instantaneous action changes, falling action may be more likely produce energy at high frequency components, while non-falling action may cause considerable noise disturbance at low frequency components.

Figure 3:
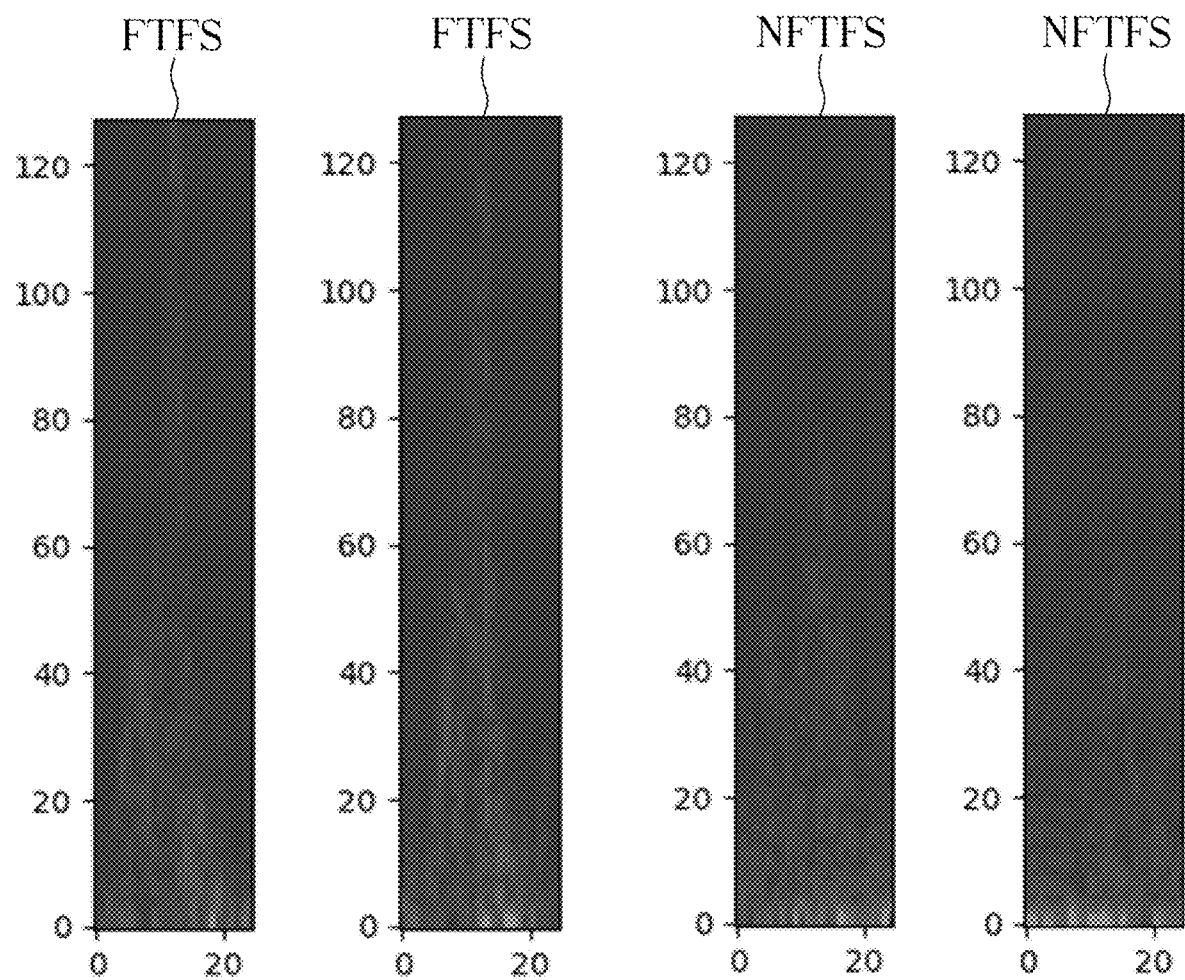
FIG. 3 is a schematic diagram of spectrograms of falling action and spectrograms of non-falling action according to an embodiment of the present disclosure.

However, please refer to FIG. 3, which is a schematic diagram of spectrograms FTFS of falling action and spectrograms NFTFS of non-falling action according to an embodiment of the present disclosure, wherein the horizontal axis is 25 time points (corresponding to 0-3.2 seconds) after the short time Fourier transform, the vertical axis is 128 frequency points (corresponding to 0-250 Hz) after short time Fourier transform, and different gray scales represent different energy intensities at corresponding time and frequency. As shown in FIG. 3, the main features of the high frequency peaks of the spectrograms FTFS of falling action are not obvious. When someone moves or bends over, etc., features of the spectrograms NFTFS of non-falling action will be similar (e.g., also with slight high frequency peaks). In such a situation, the deep learning engine may generate false positive results.

Figure 4:
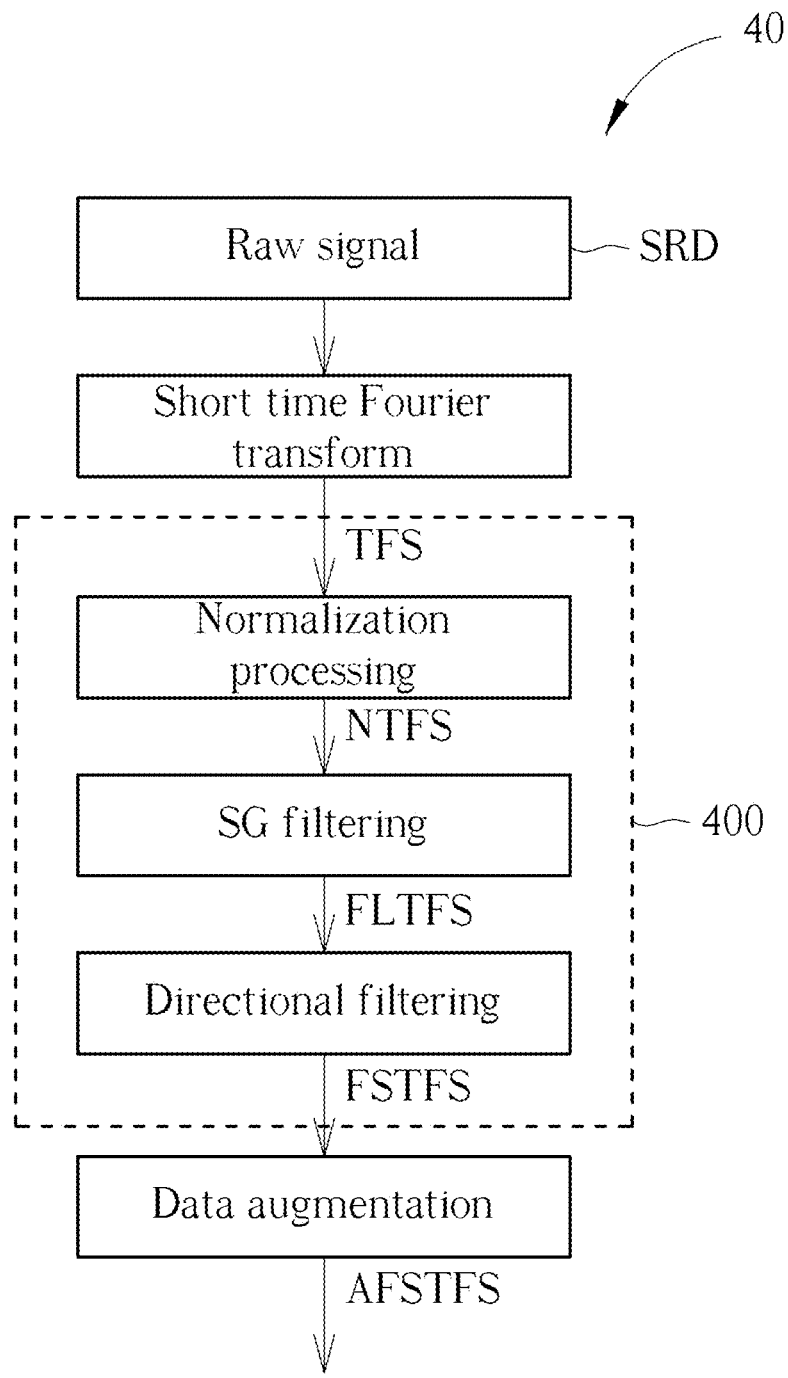
FIG. 4 is a schematic diagram of a feature enhancement and data augmentation process according to an embodiment of the present disclosure.

Please refer FIG. 4, which is a schematic diagram of a feature enhancement and data augmentation process 40 according to an embodiment of the present disclosure. The feature enhancement and data augmentation process 40 is utilized for the action detection device 10. In short, the action detection device 10 obtain at least one spectrogram TFS, then performs a feature enhancement processing 400 on the at least one spectrogram TFS, to enhance at least one feature corresponding to at least one action in the at least one spectrogram TFS and generating at least one feature enhanced spectrogram FSTFS. The feature enhancement processing 400 includes a directional filtering, and the at least one action includes a falling action.

In this case, since a feature related to falling action in the at least one feature enhanced spectrogram FSTFS is enhanced, a deep learning engine trained by the at least one feature enhanced spectrogram FSTFS may effectively and correctly identify a feature enhanced spectrogram corresponding to a falling action, and then the action detection device 10 may generate the alarm ALM accordingly. As a result, the present disclosure may enhance the feature of the falling action in the spectrogram, and improve discernment of features of different actions, to avoid false positive results.

Specifically, after obtaining the raw signal SRD through, for example, a continuous wave radar, the action detection device 10 performs short time Fourier transform (STFT) on the raw signal SRD, thereby obtaining at least one spectrogram TFS. Next, since falling action has dramatic change in velocity, there will be significant energy at high frequency component. Thus, the feature enhancement processing 400 may include a normalization processing, for normalizing the at least one spectrogram TFS along a frequency axis and generating at least one normalized spectrogram NTFS, to effectively make the features of high-frequency energy prominent.

Figure 5:
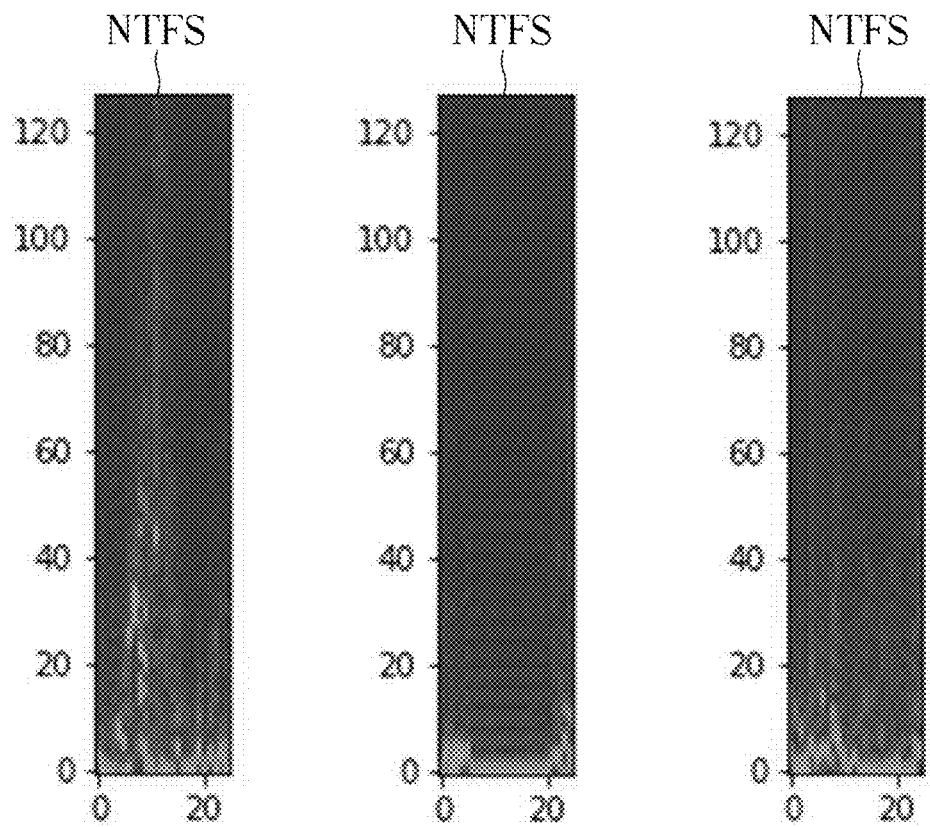
FIG. 5 is a schematic diagram of normalized spectrograms after normalization according to an embodiment of the present disclosure.

For example, please refer FIG. 5, which is a schematic diagram of normalized spectrograms NTFS after normalization according to an embodiment of the present disclosure, wherein the normalized spectrograms NTFS from left to right are corresponding to falling action, non-falling action, and non-falling action that is prone to trigger false alarms. As shown in FIG. 5, after the at least one spectrogram TFS is normalized along the frequency axis (i.e. the strongest energy is set to 1 and the weakest energy is set to 0 for each frequency axis corresponding to each time point), the high-frequency energy in the central time point (where falling occurs) is prominent, which is different from the spectrogram FTFS of falling operation illustrated in FIG. 3 where energy of low frequency noise in other time points is relatively stronger to cause the high-frequency energy in the central time point not prominent.

Please continue to refer to FIG. 4, the feature enhancement processing 400 may include a Savitzky-Golay (SG) filtering, for performing smoothing and noise reduction on the normalized spectrogram NTFS and generating at least one filtered spectrogram FLTFS (in other embodiments, the feature enhancement processing 400 may not include the normalization processing, such that the SG filtering directly performs smoothing and noise reduction on the at least one spectrogram TFS and generates at least one filtered spectrogram FLTFS). In detail, the SG filtering may emphasize the changes in the energy profile of the spectrogram (that is, the energy generated by action), rather than the intensity changes due to random vibrations caused by noise. The SG filtering is widely used in data smoothing and noise reduction in this field, and is a filtering method according to local polynomial least squares fitting in the time domain. The feature of the SG filtering is ensuring the shape and width of the signal unchanged while filtering out noise. Two main parameters of the SG filtering are window length and order of the fitting polynomial. The window length decides the number of samples referred by each filtering processing. The larger the window size, the better the smoothing effect. The higher the order of the polynomial, and the higher the degree of fitting with original data. Since the normalized spectrum NTFS or the at least one spectrogram TFS includes noise components, if the order of the SG filtering is too high to over-fit noise components, the deep learning engine may misjudge the variation caused by the noise is a strong feature. Therefore, it is necessary to appropriately design the window length of the SG filtering and the order of the fitting polynomial.

Figure 6:
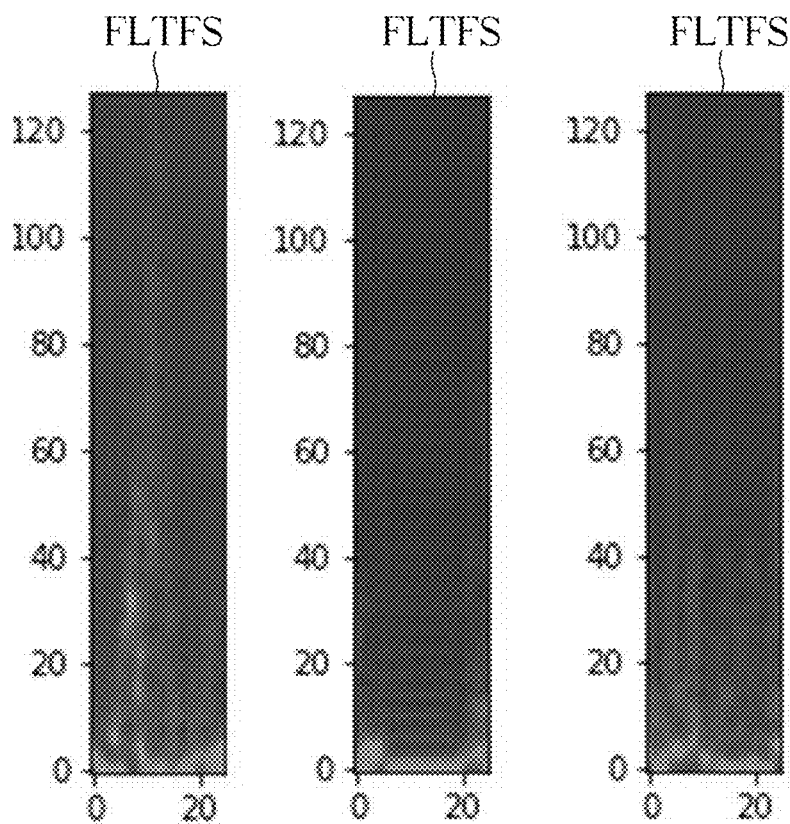
FIG. 6 is a schematic diagram of filtered spectrograms after filtering according to an embodiment of the present disclosure.

For example, please refer to FIG. 6, which is a schematic diagram of filtered spectrograms FLTFS after filtering according to an embodiment of the present disclosure, wherein the filtered spectrograms FLTFS from left to right are corresponding to falling action, non-falling action, and non-falling action that is prone to trigger false alarms. As shown in FIG. 6, this embodiment utilizes a window size of 9 and an order of 5 as parameters of the SG filtering. The preferred parameters obtained from experiments make the filtered spectrogram FLTFS maintain the feature of the normalized spectrogram NTFS while reducing noise energy under finite smoothing.

Please continue to refer to FIG. 4. In the feature enhancement process 400, the directional filtering may filter each of the at least one filtered spectrogram FLTFS along at least one direction and generate each corresponding set of at least one directional filtered spectrogram DFLTFS, and utilizes a most energy significant one among the each of the at least one filtered spectrogram FLTFS and the each corresponding set of at least one directional filtered spectrogram DFLTFS as a corresponding feature enhanced spectrogram FSTFS (in other embodiments, the feature enhancement processing 400 may not include the normalization processing and the SG filtering, so that the directional filtering directly filters each of the at least one spectrogram TFS along at least one direction and generate each corresponding set of at least one directional filtered spectrogram DFLTFS, and utilizes a most energy significant one among the each of the at least one spectrogram TFS and the each corresponding set of at least one directional filtered spectrogram DFLTFS as a corresponding feature enhanced spectrogram FSTFS).

Figure 7:
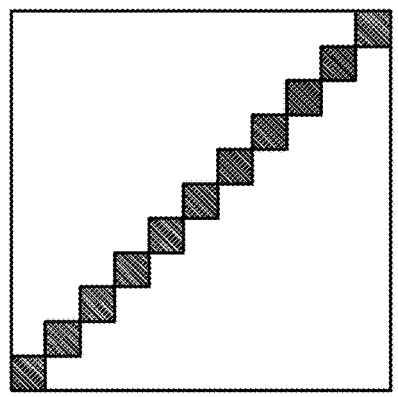
FIG. 7 is a schematic diagram of windows with different filtering directions according to an embodiment of the present disclosure.
Figure 7:
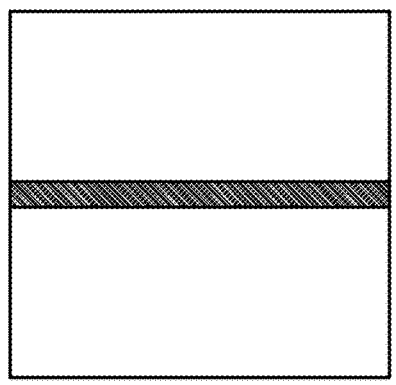
Figure 7:
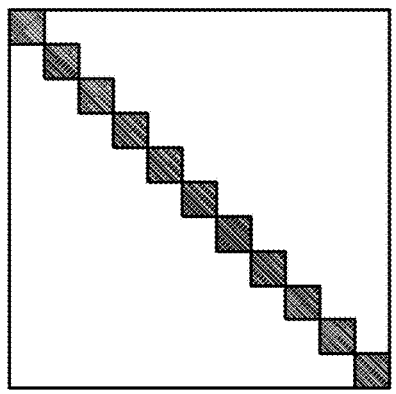
Figure 7:
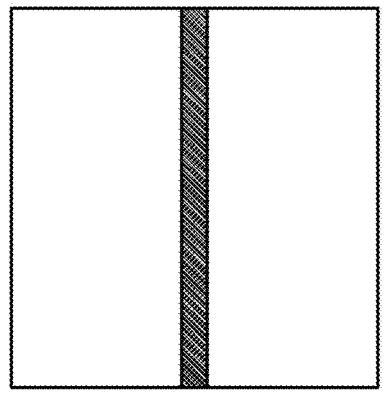

In detail, in the application of radar wave for falling detection, the energy of the falling action has an instantaneous energy response at high frequency component, and the response is most significant in a direction of 90° in the spectrogram TFS. Environmental noise will be more concentrated in the low frequency component, and has corresponding energy response along the horizontal axis in the spectrogram TFS, such that the response is significant in a direction of 0°. In this case, please refer FIG. 7, which is a schematic diagram of windows with different filtering directions according to an embodiment of the present disclosure, wherein the windows from left to right are corresponding to filtering directions of 0°, 45°, 90° and 135°. As shown in FIG. 7, different windows have different directions, and therefore after the spectrogram TFS is convoluted with each window (i.e., each window is applied to each point of the spectrogram TFS to generate each new value), the generated directional filtered spectrogram DFLTFS is more prominent in the corresponding direction. In the present embodiment, windows with the size of 5*5 are applied in the directional filtering to adapt to the instantaneous falling spectrogram, and energy at each time point of the original filtered spectrogram FLTFS and 4 directional filtered spectrograms DFLTFS after directional filtering are performed with binary classification, such that a time point with energy greater than a noise threshold is set to 1, otherwise a time point is set to 0. The most energy significant one (among the original filtered spectrogram FLTFS and the 4 directional filtered spectrograms DFLTFS) having the most number of time points with energy greater than the noise threshold in a corresponding spectrogram energy histogram is utilized as the feature enhanced spectrogram FSTFS, which means that the one with strongest feature is utilized as the final feature enhanced spectrogram FSTFS.

Figure 8:
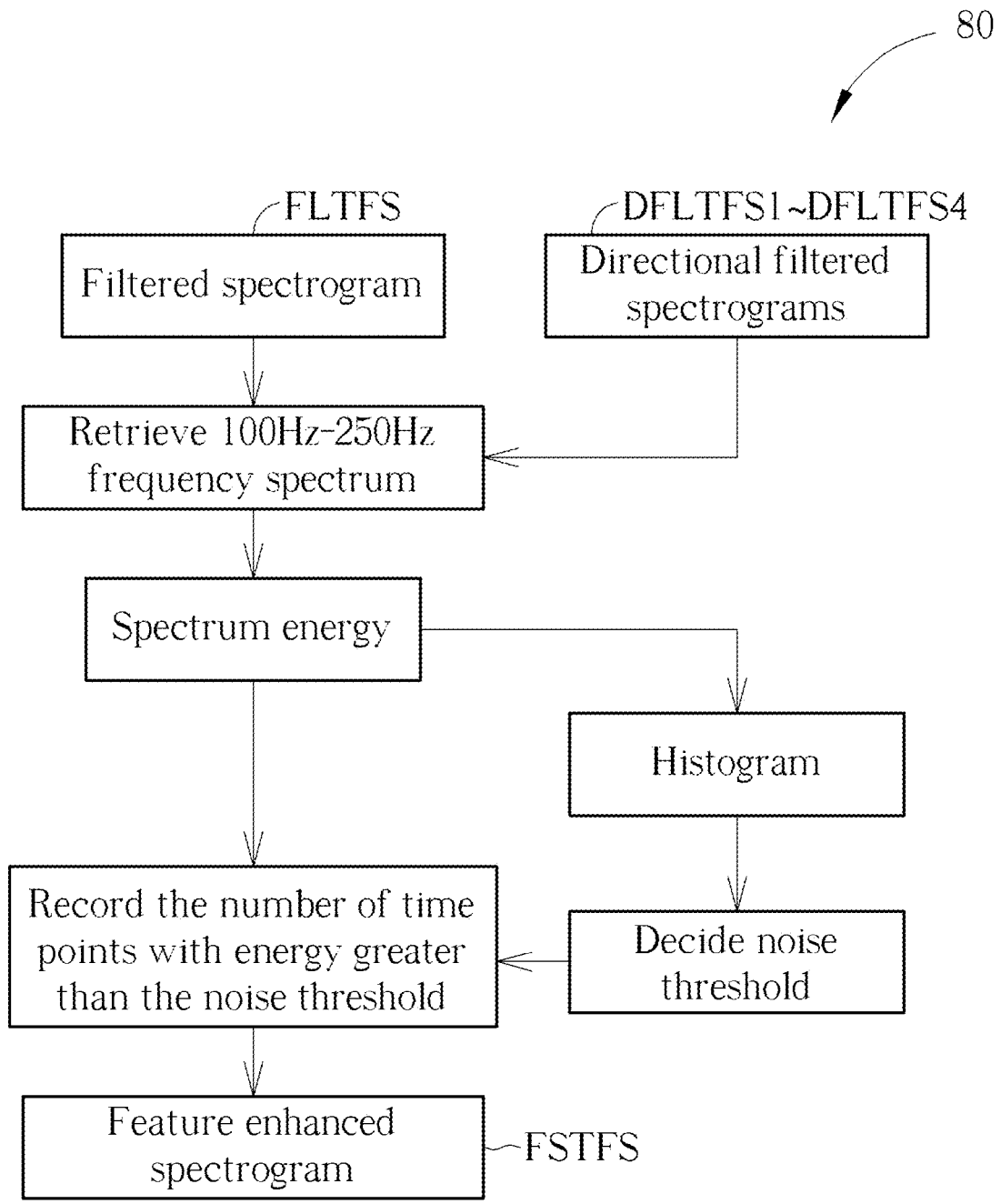
FIG. 8 is a schematic diagram of a feature enhancement process according to an embodiment of the present disclosure.
Figure 9:
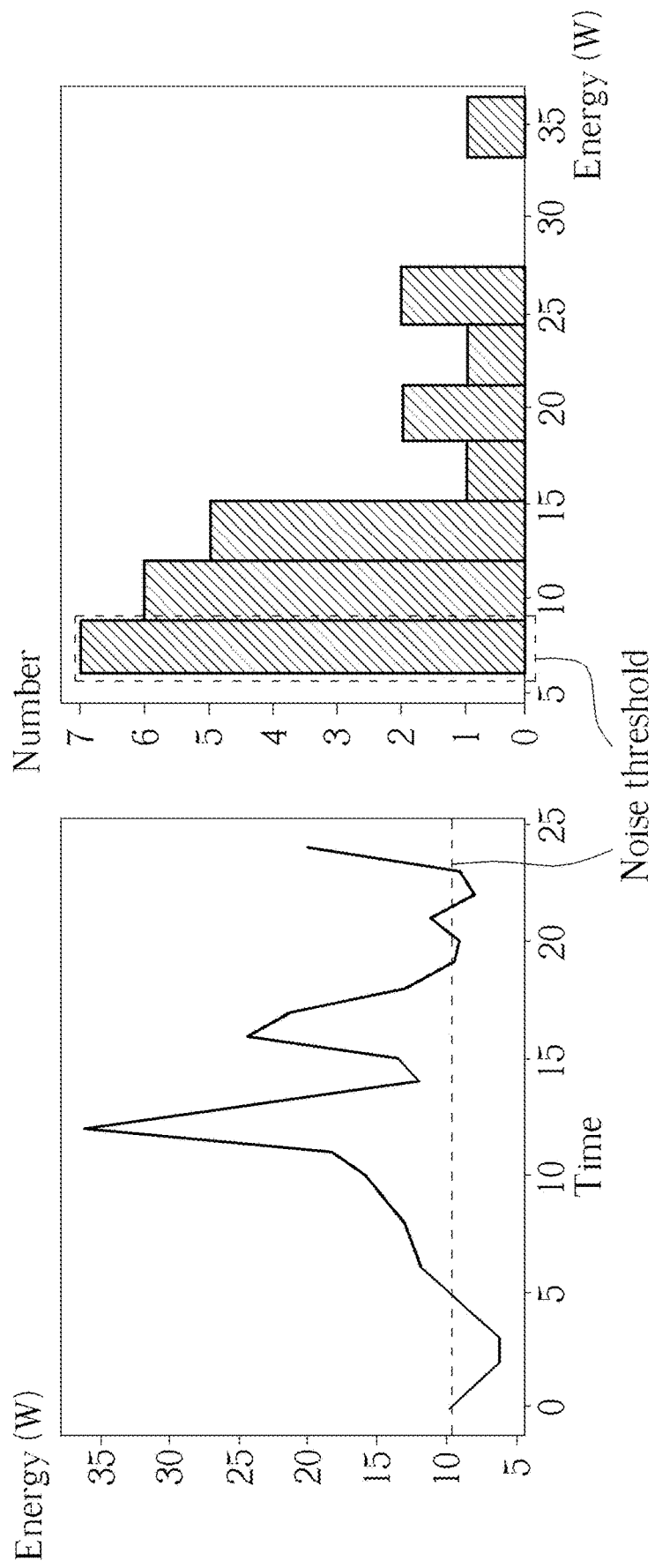
FIG. 9 is a schematic diagram of spectrum energy and a spectrum energy histogram according to an embodiment of the present disclosure.

Specifically, please refer FIG. 8 and FIG. 9. FIG. 8 is a schematic diagram of a feature enhancement process 80 according to an embodiment of the present disclosure, and FIG. 9 is a schematic diagram of spectrum energy and a spectrum energy histogram according to an embodiment of the present disclosure. As shown in FIG. 8, after performing directional filtering on filtered spectrogram FLTFS along directions of 0°, 45°, 90° and 135° and generating directional filtered spectrograms DFLTFS1-DFLTFS4, this embodiment retrieves 100 Hz-250 Hz frequency spectrums of the filtered spectrum FLTFS and the directional filtered spectrograms DFLTFS1-DFLTFS4, and calculates the respective spectrum energies (e.g., left of FIG. 9 illustrates spectrum energies of respective time points, wherein the horizontal axis is 25 time points corresponding to 0-3.2 seconds, and the vertical axis represents energy). Afterwards, this embodiment calculates respective spectrogram energy histograms of the filtered spectrum FLTFS and the directional filtered spectrograms DFLTFS1-DFLTFS4 (e.g., right of FIG. 9 illustrates the number of time points distributed in each energy range), and then an upper bound of an energy range with a most number of time points in respective spectrogram energy histograms are taken as respective noise thresholds (for example, there are 7 time points between 6-9 watts as shown in right of FIG. 9, and the number of time points is greater than other energy ranges, which means 6-9 watts is most frequent and thus regarded as noise energy, such that 9 watts is the noise threshold). The number of time points with energy greater than the noise threshold is recorded (e.g., the number of time points with energy greater than the noise threshold as shown in FIG. 9 is 18). Finally, the most energy significant one (among the original filtered spectrogram FLTFS and the 4 directional filtered spectrograms DFLTFS1-DFLTFS4) having the most number of time points with energy greater than the noise threshold in a corresponding spectrogram energy histogram is utilized as the feature enhanced spectrogram FSTFS.

Figure 10:
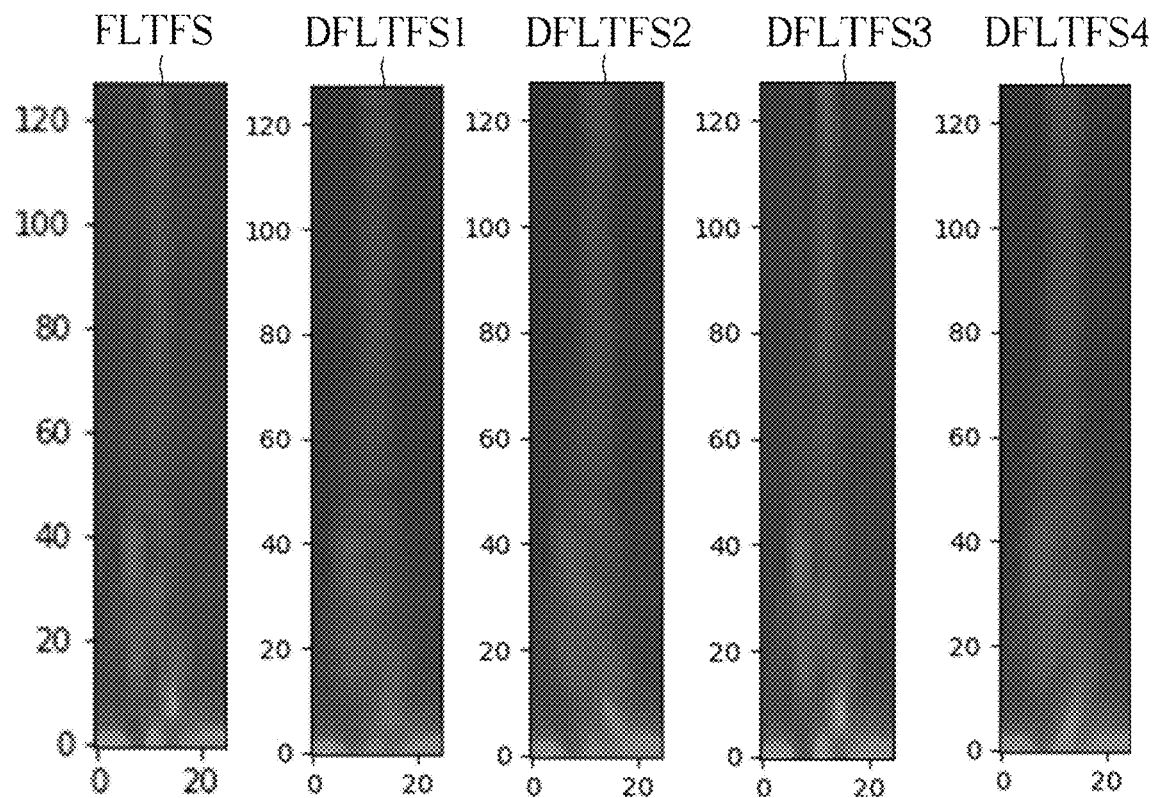
FIG. 10 is a schematic diagram of a filtered spectrogram and directional filtered spectrograms according to an embodiment of the present disclosure.

For example, please refer to FIG. 10, which is a schematic diagram of the filtered spectrogram FLTFS and the directional filtered spectrograms DFLTFS1-DFLTFS4 according to an embodiment of the present disclosure, wherein spectrograms from left to right are corresponding to no directional filtering, and filtering along directions of 0°, 45°, 90° and 135°. As shown in 10, since falling action has an instantaneous energy response at high frequency component, the directional filtered spectrograms DFLTFS3 obtained by filtering the filtered spectrograms FLTFS along a direction of 90° has more significant high-frequency energy, so that the most energy significant directional filtered spectrograms DFLTFS3 has a most number of time points with energy greater than a noise threshold in a corresponding spectrogram energy histogram, and can be utilized as the corresponding feature enhanced spectrogram FSTFS.

It is worth noting that the above embodiment enhances the feature of the falling action in the spectrogram, and improve discernment of features of different actions, to avoid false positive results. Those skilled in the art may make modifications or alterations accordingly, which are not limited to this. For example, the above embodiment enhances the feature of the falling action in the spectrogram to improve discernment from other actions. In other embodiments, corresponding features of other actions in the spectrogram may be enhanced depending on the actual needs, to increase the discernment of other actions.

Furthermore, in the above embodiment, the deep learning engine trained according to the at least one feature enhanced spectrogram FSTFS may effectively and correctly identify a feature enhanced spectrogram corresponding to a falling action. However, as shown in FIG. 4, the feature enhancement and data augmentation process 40 may perform data augmentation on the at least one feature enhanced spectrogram FSTFS first, to generate a plurality of augmented feature enhanced spectrograms AFSTFS to train the deep learning engine. A number of the plurality of augmented feature enhanced spectrograms AFSTFS is greater than a number of the at least one feature enhanced spectrogram FSTFS. As a result, the present disclosure may increase the amount of falling data via data augmentation algorithm to strengthen model generalization capability, and improve model processing capability for a variety of information to increase the effectiveness of the model.

Figure 11:
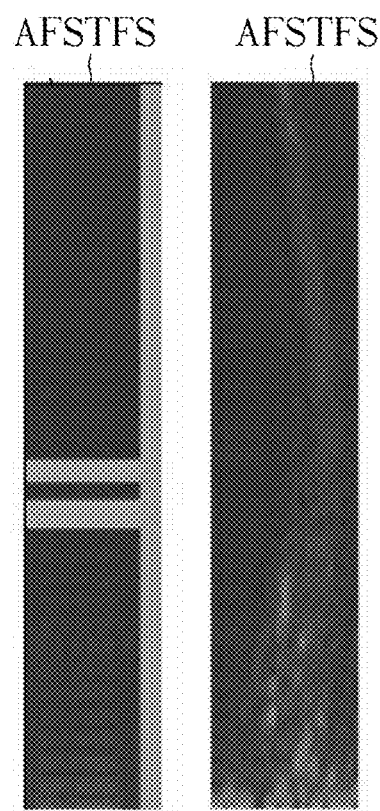
FIG. 11 is a schematic diagram of augmented feature enhanced spectrograms generated via a shielding operation and a non-linear distortion according to an embodiment of the present disclosure.

Specifically, please refer to FIG. 11, which is a schematic diagram of augmented feature enhanced spectrograms AFSTFS generated via a shielding operation and a non-linear distortion according to an embodiment of the present disclosure. After data augmentation in speech recognition, model of a deep learning engine may learn features of audio with loss and deformation on the time axis, audio with partial frequency missing, and audio with loss of partial clips, which increases processing capabilities of the trained model for such Information and also enhance the generalization capabilities of the model. Therefore, in the application for radar data, an embodiment of the present disclosure may achieve data augmentation via at least one shielding and a nonlinear distortion. In detail, as shown in right of FIG. 11, after data augmentation processing performs a nonlinear distortion on the feature enhanced spectrogram FSTFS, although the resulted augmented feature enhanced spectrogram AFSTFS is more distorted in the spectrogram, high frequency energy is still significant, which can be effectively learned and generalized.

On the other hand, the data augmentation processing performs at least one shielding on the feature enhanced spectrogram FSTFS, wherein the at least one shielding does not completely cover a main feature region of the feature enhanced spectrogram FSTFS. For example, as shown in left of FIG. 11, the data augmentation processing may randomly perform one time axis shielding and two frequency axis shielding which do not completely cover the main feature region. Since the radar data is retrieved leftward and rightward from the energy burst point as the center, a center of the time-domain is the main feature region. Besides, it is undesirable to over shield the frequency domain (e.g., total shielding length is desirable to be less than 30%) to cover the main feature region. Therefore, the time axis shielding is preferable to randomly shield only the left third or right third of the time domain, and the total shielding length of the two frequency axis shielding is preferably not more than 15% of the total frequency band.

In this case, speech recognition and radar wave for falling detection both utilize spectrograms for machine learning. Because the input of sound includes a variety of noises, it may be regarded as a few words are missing when people speak or words are not clearly pronounced, where people can still recognize the meaning of the sentence according to the context. Similarly, the radar wave also includes a variety of environmental noises (such as arm waving, object falling, etc.) which will cause disturbance to radar wave. In a situation that these events happen alone or together with falling action, if a falling action still needs to be identified, the model needs to have learned generalized feature of events by trained with data which is partially missing or changed.

For example, the original collected training set data only includes 1613 pieces of falling data and 11299 pieces of non-falling data. After data augmentation, the augmented training data set includes 4839 pieces of falling data and 11299 pieces of non-falling data. After a depth learning engine is trained by the augmented training data set to obtain a model and applied in an environment of a bedroom of an elderly living alone in practice, all 75 falling events have been identified, and there is no missing report and no false negative results. There are only 6 false positive (false alarms) in 839 non-falling events. Thus, precision is 100% and recall is 99.3%.

In addition, the action detection device 10 may include a processor, a transceiver circuit, and a storage unit. The processor is electrically connected to the transceiver circuit and the storage unit, respectively. The processor may be a microprocessor or an application-specific integrated circuit (ASIC). The transceiver circuit is a radar transceiver. The RF transceiver includes at least one transmitting antenna and/or at least one receiving antenna, an oscillator, a mixer, a digital to analog converter (DAC), an analog to digital converter (ADC), etc. The storage unit may be any data storage device for storing a code. The processor reads and executes the code, to execute each step of the feature enhancement and data augmentation process 40. The storage unit may be subscriber identity module (SIM), read-only memory (ROM), random-access memory (RAM), CD read-only memory (CD-ROM), magnetic tapes, floppy disk, optical data storage device, etc., but is not limited to these.

In another embodiment of the present disclosure, a transmission module of the action detection device 10 transmits the aforementioned raw signal SRD or the aforementioned spectrogram TFS to an edge device or a server. Then, the edge device or the server performs the aforementioned feature enhancement and data augmentation process 40. The edge device or the server may receive multiple aforementioned raw signals SRD or multiple aforementioned spectrograms TFS from multiple action detection devices 10.

On the other hand, the feature enhancement and data augmentation process 40 may be executed individually or collectively by one or more of the action detection devices 10, the edge device or the server.

In summary, the present disclosure may enhance the feature of the falling action in the spectrogram, and improve discernment of features of different actions, to avoid false positive results. Besides, the present disclosure may increase the amount of falling data via data augmentation algorithm to strengthen model generalization capability, and improve model processing capability for a variety of information to increase the effectiveness of the model.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A feature enhancement and data augmentation method, for an action detection device, configured for detecting the at least one action of at least one tested subject, the feature enhancement and data augmentation method comprising:
    obtaining, by the action detection device, at least one spectrogram; and
    performing, by the action detection device, a feature enhancement processing on the at least one spectrogram, to enhance at least one feature corresponding to the at least one action in the at least one spectrogram and generate at least one feature enhanced spectrogram;
    wherein the feature enhancement processing comprises a directional filtering.

2. The feature enhancement and data augmentation method of claim 1 further comprises:
    processing at least one radar reflected radio-frequency signal, to obtain the at least one spectrogram, wherein the at least one action comprises a falling action.

3. The feature enhancement and data augmentation method of claim 1, wherein the feature enhancement processing comprises a normalization processing, for normalizing the at least one spectrogram along a frequency axis and generating at least one normalized spectrogram.

4. The feature enhancement and data augmentation method of claim 1, wherein the feature enhancement processing comprises a Savitzky-Golay (SG) filtering, for performing smoothing and noise reduction on the at least one spectrogram and generating at least one filtered spectrogram.

5. The feature enhancement and data augmentation method of claim 1, wherein the directional filtering filters each of the at least one spectrogram along at least one direction and generates each corresponding set of at least one directional filtered spectrogram, and utilizes a most energy significant one among the each of the at least one spectrogram and the each corresponding set of at least one directional filtered spectrogram as a corresponding feature enhanced spectrogram.

6. The feature enhancement and data augmentation method of claim 5, wherein the most energy significant one has a most number of time points with energy greater than a noise threshold in a corresponding spectrogram energy histogram.

7. The feature enhancement and data augmentation method of claim 6, wherein the noise threshold is an upper bound of an energy range with a most number of time points in the corresponding spectrogram energy histogram.

8. The feature enhancement and data augmentation method of claim 1 further comprising:
    processing at least one radar reflected radio-frequency signal, to obtain the at least one spectrogram; and
    performing data augmentation on the at least one feature enhanced spectrogram, to generate a plurality of augmented feature enhanced spectrograms to train a deep learning engine;
    wherein a number of the plurality of augmented feature enhanced spectrograms is greater than a number of the at least one feature enhanced spectrogram.

9. The feature enhancement and data augmentation method of claim 8 further comprising:
    performing a non-linear distortion on the at least one feature enhanced spectrogram.

10. The feature enhancement and data augmentation method of claim 8 further comprising:
    performing at least one shielding on the at least one feature enhanced spectrogram, wherein the at least one shielding does not completely cover a main feature region of the at least one feature enhanced spectrogram.

11. An action detection device, for detecting the at least one action of at least one tested subject, comprising:
    a processor, for executing a program; and
    a storage unit, coupled to the processor, for storing the program; wherein the program is utilized for instructing the processor to perform following steps of:
    obtaining at least one spectrogram; and
    performing a feature enhancement processing on the at least one spectrogram, to enhance at least one feature corresponding to the at least one action in the at least one spectrogram and generate at least one feature enhanced spectrogram;
    wherein the feature enhancement processing comprises a directional filtering.

12. The action detection device of claim 11 further comprises:
    a radar transceiver circuit, coupled to the processor, for receiving at least one radar reflected radio-frequency signal, and processing the at least one radar reflected radio-frequency signal to obtain a raw signal, wherein the processor converts the raw signal, to obtain at least one spectrogram;
    wherein the at least one action comprises a falling action.

13. The action detection device of claim 11, wherein the feature enhancement processing comprises a normalization processing, for normalizing the at least one spectrogram along a frequency axis and generating at least one normalized spectrogram.

14. The action detection device of claim 11, wherein the feature enhancement processing comprises a Savitzky-Golay (SG) filtering, for performing smoothing and noise reduction on the at least one spectrogram and generating at least one filtered spectrogram.

15. The action detection device of claim 11, wherein the directional filtering filters each of the at least one spectrogram along at least one direction and generates each corresponding set of at least one directional filtered spectrogram, and utilizes a most energy significant one among the each of the at least one spectrogram and the each corresponding set of at least one directional filtered spectrogram as a corresponding feature enhanced spectrogram.

16. The action detection device of claim 15, wherein the most energy significant one has a most number of time points with energy greater than a noise threshold in a corresponding spectrogram energy histogram.

17. The action detection device of claim 16, wherein the noise threshold is an upper bound of an energy range with a most number of time points in the corresponding spectrogram energy histogram.

18. The action detection device of claim 11 further comprises:
a radar transceiver circuit, coupled to the processor, for receiving at least one radar reflected radio-frequency signal, and processing the at least one radar reflected radio-frequency signal to obtain a raw signal, wherein the program further instructs the processor to perform following steps of:
converting the raw signal, to obtain the at least one spectrogram; and
performing data augmentation on the at least one feature enhanced spectrogram, to generate a plurality of augmented feature enhanced spectrograms to train a deep learning engine;
wherein a number of the plurality of augmented feature enhanced spectrograms is greater than a number of the at least one feature enhanced spectrogram.

19. The action detection device of claim 18, wherein the program further instructs the processor to perform following steps of:
performing a non-linear distortion on the at least one feature enhanced spectrogram.

20. The action detection device of claim 18, wherein the program further instructs the processor to perform following steps of:
performing at least one shielding on the at least one feature enhanced spectrogram, wherein the at least one shielding does not completely cover a main feature region of the at least one feature enhanced spectrogram.

* * * * *